United States Patent
Sercheli et al.

(10) Patent No.: US 10,913,705 B2
(45) Date of Patent: Feb. 9, 2021

(54) IRON AMINO ACID COMPOUNDS, METHOD FOR PREPARING IRON AMINO ACID COMPOUNDS, COMPOSITIONS CONTAINING IRON AMINO ACID COMPOUNDS, AND USES THEREOF

(71) Applicant: NPA—NÚCLEO DE PESQUISAS APLICADAS LTDA, Jaboticabal (BR)

(72) Inventors: Ricardo Da Silva Sercheli, Jaboticabal (BR); Nelson Henriques Fernandes, Jaboticabal (BR); Nelson Henriques Fernandes Filho, Jaboticabal (BR)

(73) Assignee: NPA—NÚCLEO DE PESQUISAS APLICADAS LTDA, Jaboticabal—SP (BR)

(*) Notice: Subject to any disclaimer, the term of this patent is extended or adjusted under 35 U.S.C. 154(b) by 291 days.

(21) Appl. No.: 15/524,587

(22) PCT Filed: Nov. 5, 2015

(86) PCT No.: PCT/BR2015/050203
§ 371 (c)(1),
(2) Date: May 4, 2017

(87) PCT Pub. No.: WO2016/070257
PCT Pub. Date: May 12, 2016

(65) Prior Publication Data
US 2018/0370903 A1     Dec. 27, 2018

Related U.S. Application Data

(60) Provisional application No. 62/077,050, filed on Nov. 7, 2014.

(51) Int. Cl.
| | | |
|---|---|---|
| *C07C 229/76* | (2006.01) |
| *A61K 31/295* | (2006.01) |
| *C07C 229/08* | (2006.01) |
| *C07C 321/14* | (2006.01) |
| *C07C 229/24* | (2006.01) |
| *C07C 59/255* | (2006.01) |
| *C07C 59/245* | (2006.01) |
| *C07C 59/265* | (2006.01) |
| *C07C 59/08* | (2006.01) |
| *C07D 207/16* | (2006.01) |
| *A23L 33/165* | (2016.01) |
| *A23L 33/175* | (2016.01) |
| *A23C 9/13* | (2006.01) |
| *A23C 9/152* | (2006.01) |
| *A23G 3/44* | (2006.01) |
| *A23L 2/52* | (2006.01) |

(52) U.S. Cl.
CPC .......... *C07C 229/76* (2013.01); *A23C 9/1322* (2013.01); *A23C 9/1526* (2013.01); *A23G 3/44* (2013.01); *A23L 2/52* (2013.01); *A23L 33/165* (2016.08); *A23L 33/175* (2016.08); *A61K 31/295* (2013.01); *C07C 59/08* (2013.01); *C07C 59/245* (2013.01); *C07C 59/255* (2013.01); *C07C 59/265* (2013.01); *C07C 229/08* (2013.01); *C07C 229/24* (2013.01); *C07C 321/14* (2013.01); *C07D 207/16* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,067,994 A | 1/1978 | Anderson et al. |
| 7,022,351 B2 | 4/2006 | Abdel-Monem et al. |
| 2005/0064071 A1 | 3/2005 | Baldwin et al. |
| 2006/0134227 A1* | 6/2006 | Bortz ..................... A61K 31/19 424/646 |

FOREIGN PATENT DOCUMENTS

| | | |
|---|---|---|
| BR | PI0706620 A2 | 4/2011 |
| BR | PI1104374 A2 | 5/2014 |
| PT | 2717713 E | 9/2015 |

OTHER PUBLICATIONS

Elizabathe et al, "Iron(III) Amino Acid Complexes: Evidence for the Existence of a Spin Equilibrium," Polyhedron, 1987, pp. 969-974, vol. 6, No. 5.
International Search Report and Written Opinion issued in PCT/BR2015/050203 dated Jan. 28, 2016.
Puri et al, "Preparation and Properties of Tri-µ3-Oxo-Triaquotris(L-Amino Acid) Tris(Dihydrogen Phosphito)triiron(III) Nitrates: Synthetic Probes for the Ferritin Iron Core," Inorganica Chimica Acta, 1982, pp. 49-56, vol. 66.
Tucker et al, "Preparation and Properties of Fe3+-Amino Acid Complexes," Archives of Biochemistry and Biophysics, 1975, pp. 433-438, vol. 166.

* cited by examiner

*Primary Examiner* — Clinton A Brooks
(74) *Attorney, Agent, or Firm* — Arent Fox, LLP

(57) ABSTRACT

The invention describes hydrosoluble iron (III) oxyhydroxide complexes prepared from different sources of iron, amino acids and carboxylic acids. The iron (III) complexes have no undesirable residual taste and can be used as supplementation forms for the prevention or treatment of iron deficiency anemia in humans or animals and pharmaceutical or food compositions containing them.

12 Claims, No Drawings

IRON AMINO ACID COMPOUNDS, METHOD FOR PREPARING IRON AMINO ACID COMPOUNDS, COMPOSITIONS CONTAINING IRON AMINO ACID COMPOUNDS, AND USES THEREOF

CROSS-REFERENCE TO RELATED APPLICATIONS

This application is a National Stage entry of International Application No.: PCT/BR2015/050203, filed Nov. 5, 2015, which claims priority to U.S. Provisional Application No. 62/077,050, filed Nov. 7, 2014. The disclosure of the priority applications are hereby incorporated in their entirety by reference.

FIELD OF THE INVENTION

The present invention relates to the field of chemistry and more specifically to the field of chemistry applied to iron complexes of water soluble amino acids, processes for preparing these complexes, the use of the complexes as a way of supplementation for the prevention or treatment of iron deficiency anemia in humans or animals, and food or pharmaceutical compositions containing them.

STATE OF THE ART

Iron deficiency is one of the most common causes of anemia and may be the most frequent nutritional deficiency in the world, affecting a significant portion of the world population. Iron deficiency is mainly caused by the lack of this mineral in the diet or low iron absorption in the body and, in addition to contributing to anemia, also alters other physiological conditions.

The clinical manifestations of iron deficiency can be even more pronounced during growth, pregnancy and menstruation, and affect up to seven times more women than males. For these reasons, it is currently very common to use iron supplements for fortification of processed foods or as components for preparing pharmaceutical or food compositions, alone or in combination with other nutrients.

There are several compounds presently available for the supplementation of iron that can be selected from inorganic or organic forms such as pyrophosphates, sulfates, complex sugars or polysaccharides, gluconates, citrates, and amino acid chelates, among others. However, the use of these compounds can result in changes in the organoleptic properties of the processed food or in unwanted interactions with other components of formulations containing them, limiting the use of these forms of iron in desired applications.

More specifically, iron is perhaps the nutrient that offers most challenges for the preparation of food or pharmaceutical compositions, as it normally results in the appearance of undesirable flavors and coloring when incorporated into processed foods or medicine and causes decomposition of other components present in the pharmaceutical formulations, such as vitamins.

In general, the addition of iron in formulations limits their development, since many desirable nutrients or certain additives permitted in food and drugs, such as flavors and colors, may not be associated with this mineral.

Conceptually, the forms of iron which are commercially available can be classified into two groups: (i) iron forms which have high solubility and, consequently, higher bioavailability and lower stability in formulations, and (ii) iron forms that exhibit low solubility and, consequently, lower bioavailability and increased stability in formulations. Thus, one way to minimize unwanted interactions is the use of less bioavailable forms of iron, which in some cases promote an increase in the stability of the formulations.

Unfortunately, the commercially available water soluble forms of iron have a metallic taste as one of their main drawbacks, considered very unpleasant or disgusting. This aspect is discussed in the technique where alternatives are shown to avoid the metallic taste inherent in iron compounds, which have so far failed to effectively solve the problem. This can be verified experimentally or in descriptions found in the art, such as in the patent application BRPI 9508746, where the inventors show that iron forms classified as amino acid chelates have to be taken in capsules or other means to prevent the inherent metallic compound taste. In this document, the inventors teach how to improve the taste of amino acid chelates, but make it clear that "this is not to say that a flavor or taste is completely lacking to taste-free amino acid chelates."

In document U.S. Pat. No. 6,461,651 B1, the inventors teach how to prepare calcium salts and magnesium chelates of Fe (III) EDTA. However, it is apparent from the examples of the process for the preparation of chelates and their use in fortified foods, that the compounds have low solubility in water, which is also not desired for compounds used for the administration of iron. Said document, however, is not capable of discussing or solving the issue of the undesired residual taste that the claimed compounds confer on processed foods, a feature inherent in EDTA iron chelate salts. From said document, it is not possible to predict that the claimed compounds do not impart an undesirable residual taste to processed foods, a feature inherent in EDTA iron chelate salts.

Other forms of iron used for nutritional or therapeutic purposes are prepared from saccharides or derivatives thereof and are referred to as iron carbohydrate complexes. Compounds of this class include oxides and hydroxides of iron (III) coordinated with polyhydroxy compounds such as dextran, polymaltose, sucrose, gluconic acid, among others, with or without the sodium ion present in their structure. Such substances are characterized in that they are in the form of a plurality of iron (III) complexes or agglomerates associated to the formation of macromolecules that may have an average molecular weight distribution of up to 600 kDa. In these complexes, oxides and hydroxides of iron (III) are stabilized by carbohydrates which keep the iron species in solution.

The complexes of iron oxyhydroxides currently available are classified into different types and are characterized by having several limitations. Class I complexes include iron dextran and iron dextrin and are known to cause anaphylactic reactions during treatment. Type II complexes include compounds of intermediate stability and strength, such as iron saccharate, which have low solubility. Type III complexes comprising labile and weak iron compounds, such as iron (III) gluconate, iron (III) citrate and iron (III) sorbitol. Type IV complexes comprise mixtures of at least two complexes of different classes and, considering their iron distribution patterns, none can be considered clinically safe. In such cases, toxic reactions might be expected even at lower therapeutic doses and, thus, intravenous use is not recommended.

Those skilled in the art will recognize that the steps of synthesis, isolation and purification of soluble iron oxyhydroxide complexes are characterized by a notable difficulty.

Therefore, various protocols for their preparation are described which often still lead to the obtaining of products which are not very stable.

As can be seen, the processes described in the prior art for obtaining soluble complexes of iron oxyhydroxides always involve the use of saccharides and synthetic steps undesirable for their activation.

The processes are characterized by the formation of possibly toxic by-products and the need for use of difficult-to-handle and obviously hazardousness reagents, such as bromine derivatives and activated chlorine salts. In other cases, the undesired combination of several steps, such as hydrolysis and reduction of saccharides, is required in addition to ultrafiltration for the isolation of products in certain molecular weight ranges.

In still other cases, the processes described in the prior art use known toxic organic solvents for the isolation of the products, such as methanol. In other cases it is still necessary to use derivatives of carbohydrates that have a high associated cost or other substances that are not permitted in food.

Commercially available complexes of iron oxyhydroxides are also characterized by being stable in solution only when presented in high concentrations. In this specification, it is understood that solutions at high concentrations relate to solutions which have iron contents greater than or equal to 1 mg Fe (III)/ml, and the term stable refers to formulations which have the iron in the form of solutions without the occurrence of precipitates that can be retained in meshes of 0.2 microns.

Unfortunately, this feature also limits the administration of these products through liquid food carriers such as juices, milk beverages and milk, among others, since the nutritional requirements of iron mandate the preparation of fortified food compositions with levels of iron normally below 0.1 mg/ml.

Limitations for food use of currently available iron oxyhydroxide complexes are even more evident if they are considered to be used primarily in parenteral applications, with the only iron compound of this class designated by the World Health Organization Guidelines on Food Fortification With Micronutrients of the World Health Organization and Food and Agriculture Organization of the United Nations (2006)) for oral administration for correction of nutritional deficiencies being Fe (III) saccharate.

Unfortunately, Fe (III) saccharate is classified as a compound with very low solubility in water and is related to ferrous fumarate and ferrous succinate, compounds known to be insoluble in food formulations, as verified in R F Hurrell Preventing Iron Deficiency Through Food fortification, Nutrition Reviews, 55, 1997, 210-222.

The inherent insolubility of Fe (III) saccharate promotes fewer organoleptic problems in formulations as compared to free soluble iron compounds in water. However, it concomitantly presents lower comparative bioavailability and limits its application in food compositions, since it cannot be used in an ideal way in liquid presentations.

The reasons apparent to those skilled in the art related to such limitations, range from the difficulty in obtaining homogeneous distributions of the iron source in the food compositions used as the carrier, to obtaining undesirably heterogeneous final products.

In general, iron administration in the form of Fe (III) saccharate by carriers selected from liquid food presentations such as drinks, syrups, juices, milk, milk compositions and yogurt, among others is disadvantageous. In these cases, iron supplementation is preferentially made with soluble iron compounds, which causes an undesirable organoleptic alteration in the products and, mainly, changes in taste and color. For example, ferrous sulfate, ferrous lactate, ferrous gluconate and ferric ammonium citrate as well as the less soluble forms ferrous fumarate and ferric citrate produce undesired coloration when added to chocolate milk drinks.

Taste changes may be directly related to the metallic taste of iron inherent in the commercially available forms, particularly in beverages, but may also be caused by the oxidation of fats present in food compositions in iron catalyzed reactions, occurring during the storage period of the food, which reduces its shelf life.

As shown above, the description of new iron compounds that may have greater advantages than those described in the prior art to date are of great interest. More specifically, the description of iron compounds which may be characterized by having high solubility and comparative bioavailability, and which do not present the characteristic undesirable metallic taste of soluble forms of iron intended for mineral supplementation, are of great interest. Also of great interest is the description of iron compounds which do not cause a significant change in the composition of the media used as carriers for their administration, to the extent of resulting in changes in their organoleptic properties. In addition, it is also of great interest to describe iron compounds which exhibit high comparative stability, so as to enable their administration through food carriers, such as beverages, milks, juices, beverage preparations and solid foods, among others. Thus, it is of great interest to describe alternatives that circumvent the technical problem contained in the descriptions mentioned above.

SUMMARY OF THE INVENTION

The present invention relates to iron compounds with excellent palatability that also have high solubility and stability. More particularly such compounds include iron oxyhydroxides coordinated with ligands which are selected solely between essential and nonessential amino acids, organic acids and their salts. A second embodiment of the present invention is the procedure for obtaining such compounds. A third embodiment of the present invention relates to pharmaceutical and/or food compositions comprising the iron compound hereby obtained. Finally, the present invention relates to the use of such compounds and/or compositions in the preparation of a medicine or as a dietary supplement for the prevention and/or treatment of iron deficiency anemia in humans or animals.

DETAILED DESCRIPTION OF THE INVENTION

The present invention relates to iron compounds with excellent palatability and that also have high solubility and stability. More particularly, such compounds include Fe (III) oxyhydroxides coordinated with ligands.

The compound formed comprising essential or non-essential amino acids and carboxylic acids, ionized or not, are coordinated by various interactions with iron oxyhydroxides. For a better understanding of the invention only, such compounds may also be referred to herein as ferrous amino acid complexes.

The iron complexes of amino acids described in this invention differ totally from substances comprising complexes of iron (III) oxyhydroxides so far known in the art.

One of the main differences of the present compounds with respect to the prior art consists in the fact that the compounds described herein are not prepared with or contain in their composition carbohydrates or any of their derivatives. More specifically, the compounds of the present invention are not prepared with or contain substances classified as saccharides or activated or non-activated polysaccharides, such as dextrans, dextrins, dextrose, polydextrose, maltitol, maltose, glucose, sucrose, sorbitol, gluconic acid, amino saccharides or similar substances.

The iron amino acid complexes described in this invention are completely different from the substances comprising the amino acid chelates, which are a class of compounds characterized by structurally presenting a metal center coordinated with amino acids.

In the compounds of the present invention, iron is presented in the form of its possible oxyhydroxides, obtaining, thus, particular chemical structures that present different and absolutely unexpected properties for amino acid complexes containing iron.

The compounds of the present invention comprise a new class of substances which have the necessary characteristics to be used as ingredients for preparing compositions for hematinic iron administration in humans and animals.

The advantages achieved by obtaining the novel compounds are apparent to those skilled in the art, due to various reasons.

The excellent solubility of the compounds of the present invention provide that the iron complexes of amino acids can be administered in liquid carriers such as beverages, milk, ferments or syrups, without changes observed to the organoleptic properties of foods, especially in color and flavor.

The inherent characteristics of iron complexes of amino acids of the present invention, as detailed above, permit the use of such complex compositions which can be administered orally without rejection from the individual, which is a condition that is currently associated with commercially available sources of iron, thereby increasing the adherence to treatment for iron deficiency.

The use of the iron complexes described in this invention also circumvents the problems associated with the addition of iron in compositions prepared with dyes normally used for the preparation of pharmaceutical and food formulations, since it does not interact with these substances and, thus, does not cause changes in anticipated and desired colorations.

Particularly, the use of the complexes of interest of this invention also circumvents the problems associated with the addition of iron in compositions containing sensitive nutrients to commercially available sources of iron.

More specifically, compositions containing vitamins, omega 3, omega 6, omega 9 and other components of naturally occurring oils and their derivatives, are more susceptible to decomposition in the presence of iron. In this case, the use of iron complexes herein disclosed, does not cause the reduction of nutrient contents in the formulations containing them.

Another object of the invention comprises a process for obtaining the compounds of the present invention.

Another object of the invention refers to pharmaceutical and/or food compositions comprising as the main active ingredient the compounds of interest of this invention, iron (III) amino acid complexes and at least one pharmaceutically and/or nutritionally acceptable carrier.

Another object of the invention relates to the use of iron (III) amino acid complexes as mineral and/or composition forms comprising the same, in the preparation of a medicine for treating and/or preventing iron deficiency in a human individual and/or animal subject.

In the present invention, the manner of interaction between the iron (III) species with the organic molecules in the herein disclosed compounds, occurs in a manner that provides a stable arrangement, making it impossible for the species of iron (III) from agglomerating and forming insoluble precipitates in aqueous presentations.

In the compounds disclosed herein, interactions with iron (III) species occur both through the carboxylic and amino groups of the amino acids, and through the carboxylic or hydroxyl groups of the organic acids, and the coordination of the organic ligands can occur through only one, or more than one binding site, leading to the formation of cyclic structures with the iron (III) species. The compounds of the present invention are represented by Formula I.

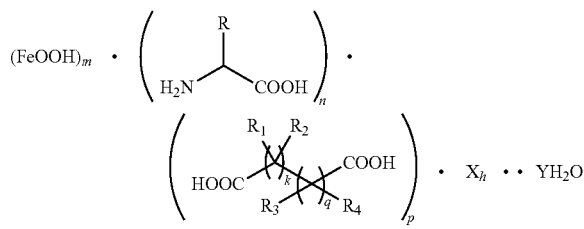

where R is equal to —H or the side chain of an essential or unessential amino acid
R1 is —H or —OH,
R2 is —H or —CH 2 COOH,
R3 is —H or —OH,
R4 is H or —OH,
k is equal to zero or 1; and
if k is equal to zero, q can vary between 1 and 3;
if k is equal to 1, q can vary between zero and three.

Alternatively, in a preferred embodiment of the present invention, when R1 and R4 do not represent a substituent, and R2 and R3 are equal to H, the selected organic acid is fumaric acid; X is equal to —Na, —K, —Ca, —Mg or —NH+ and Y may vary between 0 and 20. When m equals 1, n can vary between 0.5 and 10.0, p can vary between 0.1 and 1.0, and h can vary between 0.001 and 5.0. The iron content of the obtained amino acid complex may vary from 0.5 to 30% w/w, preferably between 10 and 20% w/w, depending on the selected binders and hydration of the prepared complexes. The molar ratio varies as follows:
m:n ranges from 1 0.5 to 1:10;
m:p ranges between 1:0.1 and 1:1;
m:h ranges between 0.001 and 5.0.

In another aspect of the invention, the process for the preparation of iron (III) amino acid complexes comprising:
(i) reaction of a source of iron (III) with an amino acid, an organic acid and a base in aqueous solution;
(ii) separating the iron (III) amino acid complex obtained in solid form or as an aqueous solution; and
(iii) drying the solvent used for obtaining the iron (III) amino acid complex.

The selected iron source can be any of the iron compounds that are commercially available, which include, but are not limited to: ferric hypophosphite, ferric albuminate, ferric chloride, ferrous chloride, ferric sulfate, ferrous sulfate, ammonium ferric sulfate, ammonium ferrous sulfate, ferric citrate, ammonium ferric citrate, ferrous gluconate, ferrous iodide, ferrous lactate, ferrous fumarate, ferric triglycinate, ferrous bisglycinate, ferrous aspartate glycinate, ferric nitrate, ferric aspartate, ferric phosphate, ferrous hydroxide, ferric hydroxide, ferrous oxide, ferric oxide, metallic iron, ferric ascorbate, ferrous formate, ferrous acetate, ferrous malate, ferrous glutamate, ferrous glycine sulphate and soluble ferric pyrophosphate, ferric subsulfate, sodium ferric citrate, iron sodium edetate, ferric formate, ammonium ferric oxalate, ferric potassium oxalate, ferric sodium oxalate, ferric peptonate, among other forms of iron, and their respective combinations.

If the selected iron source is in Fe (II) form, one of the various methods of conversion from Fe (II) to Fe (III) available in the prior art should be carried out before or during the reaction between the iron and the amino acid and the selected organic acid, so that the Fe (II) contents in the reaction medium are substantially zero or insignificant, such as Fe (II) contents of less than 0.1%, as compared to total iron content.

The amino acid may be selected from one of the essential or non-essential amino acids selected from glycine, L-lysine, L-alanine, L-phenylalanine, L-leucine, L-isoleucine, L-proline, L-hydroxyproline, L arginine, L-ornithine, L-methionine, L-aspartic acid, L-glutamic acid, L-valine, L-threonine, L-isothreonine, L-histidine, L-tryptophan, L-serine, L-glutamine, L-citrulline, or mixtures thereof or their enantiomeric forms. In a preferred embodiment of the invention the amino acid glycine is —H.

The organic acid is preferably a carboxylic acid, which can be selected from citric, oxalic, tartaric, malic, succinic, adipic, lactic, glycolic, acetic, salicylic, maleic, malonic, pectin, pectin hydrolysates or mixtures thereof. In a preferred embodiment of the invention the selected organic acid is citric acid.

The selected base refers to sources of sodium, potassium, calcium, magnesium and ammonium and, preferably, sodium.

More particularly, the reaction of step (i) occurs at a temperature in the range of 20 to 100° C. and in the presence of a base at varying pH ranges between 3.0 and 11.0. The development time of the reaction for preparing the amino acid complex may range between 10 min and 5 hours, depending on the iron source, amino acid, organic acid or base selected.

The stoichiometric ratio used between iron and the selected amino acid is not less than 1:0.5 and preferably is not greater than 1:10, respectively. More preferably, the stoichiometric ratio between iron and the selected organic acid may range between 1:0.1 and 1:1.

More particularly, the process of preparing the iron complexes of interest is performed using at least 0.5 molar equivalents of amino acid with respect to iron and at least 0.1 molar equivalents of the organic acid in relation to the iron. The amount of inorganic base used should be sufficient for the pH of the reaction medium to be maintained between 3.0 and 11.0.

In the present invention, the base is most preferably selected from potassium hydroxide, sodium hydroxide, calcium oxide, calcium hydroxide, calcium carbonate, potassium carbonate, potassium bicarbonate, sodium carbonate, sodium bicarbonate, potassium phosphate or calcium alkali, magnesium oxide, magnesium hydroxide, magnesium carbonate, ammonium hydroxide, or any one of their combinations.

The separating step of the obtained iron amino acid complex can be done in one of several usual ways by those skilled in the art, depending on the type complex of interest, as well as its intended use.

Accordingly, when it is desired to obtain the complex in the form of an aqueous solution, the separation can be done by ultrafiltration processes, nanofiltration or dialysis of the reaction medium and subsequent concentration by evaporation until a solution is obtained with the concentration of the desired complex.

In other cases, separation may be made by filtering processes.

In still other cases, when it is desired to obtain the complex in the form of a solid, the separation can be made by adding a solvent in the reaction medium in which the complex of interest has low solubility, such as ethanol.

The final drying step of the obtained iron amino acid complex can be done by one of several common forms of the art, which can be selected from among the possible industrial applications, depending on the available facilities.

Thus, the drying can be made by processes such as drying under reduced pressure in rotary dryers, in greenhouses with or without ventilation, spray dryer, flash dryer, among others.

The characterization of the compounds herein obtained by the process of the present invention was performed by spectroscopic analysis in the infrared region. The characterization of the compounds now obtained by the process of the present invention was performed by infrared spectroscopy analysis. The iron (III) amino acid complexes obtained by the process of the present invention have the goethite polymorphic phase ($\alpha$-FeOOH) and no formation of maghemite ($\gamma$-Fe2O3) or magnetite (Fe3O4) is observed.

Another aspect of the invention relates to pharmaceutical and/or food compositions comprising the iron complexes of amino acids as an active ingredient and at least one pharmaceutically and/or nutritionally acceptable carrier.

More specifically, the compositions disclosed by the present invention comprise about 0.01 to 200 mg iron/g of composition, 0.0 to 99% of a nutrient, 0.001 to 99% of a pharmaceutically or nutritionally acceptable inert carrier added in sufficient amounts to achieve the desired iron concentrations, 0.0 to 99% sweetener, 0.001 to 20% flavoring agents, 0.001 to 1% dye and 0.0 to 20%, and preferably 0.01 to 5% of at least one additive selected from antioxidants, humectants, anti-oxidants, thickeners, stabilizers, sequestrants, lubricants, preservatives and acidity regulators or combinations thereof.

The food and pharmaceutical compositions of the present invention as presented in liquid form, comprise iron oxyhydroxides in colloidal form, commonly referred to as iron hydroxides, stabilized exclusively by amino acids, organic acids and their salts in the form of at least one of the iron complexes of amino acids described in this invention in amounts that provide concentrations of 0.01 to 10% iron (III).

It is an advantage of the present invention that the compositions in the form of aqueous solutions do not present precipitates, even after storage periods of more than 2 years, and contain iron in high concentrations, which enable their commercial use exclusively in the form of their possible hydroxides, admittedly insoluble.

For a preferred embodiment of the present invention, the liquid pharmaceutical and food compositions comprise iron (III) hydroxides in amounts providing from 0.01 to 10% iron (III), 0.002 to 3% of an organic acid, 0.02 to 25% of an amino acid, 0.001 to 5% of a cation and 40 to 99.9% of water.

In addition, the food and/or pharmaceutical compositions may contain 0.001 to 99% of a nutrient, 0.001 to 99% of sweetener, 0.001 to 20% of flavoring agents, 0.001 to 1% of dyes and 0.001 to 20% of at least one selected additive between antioxidants, thickeners, stabilizers, sequestrants, lubricants, preservatives, acidity regulators or combinations thereof, colorants, sweeteners and flavorings.

Examples of carriers in the form of powders include, without limitation, maltodextrins, starch, calcium sulfate, magnesium sulfate, calcium carbonate, cellulose derivatives, lactose and its derivatives or any mixtures of such carriers, and other similar compounds.

Examples of suitable liquid carriers for preparing the compositions include, without limitation, water or mixtures of water and another carrier selected from sorbitol, xylitol, glucose, vegetable oils and their derivatives, aqueous solutions containing gums, sucrose, among other saccharides, alcohol, propylene glycol and the like in any proportion, provided that they enable the preparation of solutions of the iron amino acid complexes which may be administered orally, maintaining the indicated iron concentration limits.

Other examples of selected inert carriers include, without limitation, compositions in the form of mixtures for puddings, cake mix, bread, cereals, soups, sauces, cereal bars, chewy candies, hard candies, chewing gum, cheese, cream cheese, jellies, yogurts, fruit concentrates for the preparation of juices, yoghurts and milk drinks, syrups, carbonated and noncarbonated beverages selected from soft drinks, juices, flavored waters, beverages like nectar, mixed drinks, milk drinks, powder mixes for the preparation of beverages, hot drinks like tea and coffee or others obtained by fermentation.

Powder blends for the preparation of beverages include, but are not limited to, juices, chocolates, effervescent powder preparations, strawberry-flavored milk preparations or other flavored or non-flavored preparations which may contain milk proteins, plant proteins, animal proteins, carnitine, amino acids, protein hydrolysates, creatine, sources of minerals, vitamins, among other substances considered as nutrients.

Examples of ingredients used for preparing the compositions described above include, without limitation, glucose, sucrose, xylitol, fructose, sorbitol, other mixtures of saccharides, salt, and milk products obtained from their processing such as caseins, caseinates, whey concentrates, whey isolates, among others, water, vegetable oils, vegetable proteins, animal proteins, yeast proteins, yeast extracts, ferments, fresh fruits, processed fruits, fruit extracts, fresh vegetables, processed vegetables, vegetable extracts, vegetable powders, flour, starches, eggs and products obtained from their processing, cereals, chocolate, cocoa, and any one of their mixtures, as well as colorants, flavors and enzymes in any proportions.

Examples of nutrients that may be present in the food and pharmaceutical compositions include, without limitation, minerals, vitamins, omega 3, omega 6, omega 9 vegetable oils or their derivatives, lycopene, lutein, carnitine, creatine, plant extracts, amino acids, peptides, proteins, among other nutritionally important substances. Examples of minerals include zinc, calcium, magnesium, phosphorus, potassium, selenium, chromium, copper, manganese, cobalt, molybdenum, iodine, germanium, and mixtures thereof. Examples of vitamins include Vitamins C, A, D, E, B vitamins, vitamin K, folic acid, and mixtures thereof.

Within a further aspect of this invention, the food and pharmaceutical compositions may contain additives necessary or desired for the suitability of their intended use, such as anti-moisturizers, wetting agents, antioxidants, thickeners, stabilizers, sequestrants, lubricants, preservatives and acidity regulators. Limits of use of the additives used will be sufficient amounts to achieve the desired effect.

Examples of anti-humectants include, without limitation, calcium carbonate, microcrystalline cellulose, fatty acid salts (Ca, Na, K and NH4), sodium carbonate, sodium bicarbonate, sodium acid carbonate, magnesium carbonate, magnesium hydroxide, magnesium oxide, amorphous silicon dioxide, silica, calcium silicate, magnesium silicate, talc, sodium aluminum silicate, aluminum sodium silicate, aluminum silicate and the like.

Examples of humectants include, without limitation, sodium lactate, potassium lactate, sorbitol and sorbitol syrup, mannitol, glycerol, glycerin, xylitol, polydextrose and the like.

Examples of antioxidants include, without limitation, ascorbic acid, sodium ascorbate, calcium ascorbate, potassium ascorbate, erythorbic acid, isoascorbic acid, sodium erythorbate, sodium isoascorbate, lecithins, sodium lactate, citric acid, calcium citrate, tri-calcium citrate, esters of citric acid and fatty acids with glycerol, esters of citric acid and mono and diglycerides, and the like.

Examples of thickeners include, without limitation, gelatin, alginic acid, sodium alginate, potassium alginate, ammonium alginate, calcium alginate, agar, carrageenan and salts thereof, jatan gum, carob, guar gum, tragacanth, gum arabic, gum acacia, xanthan gum, caraia gum, gellan gum, sorbitol and sorbitol syrup, konjac gum, pectin, am idated pectin, microcrystalline cellulose, methylcellulose, hydroxypropylcellulose, methylethylcellulose, sodium carboxymethylcellulose, polydextrose and the like.

Examples of stabilizers include, without limitation, sodium caseinate, gelatin, calcium carbonate, calcium acetate, lecithin, monosodium citrate, disodium citrate, sodium citrate, trisodium citrate, potassium citrate, citrate tri-potassium, calcium citrate, citrate tri-calcium, alginic acid, sodium alginate, potassium alginate, ammonium alginate, calcium alginate, agar, carrageenan and its salts, jatai gum, locust bean, guar gum, tragacanth gum, gum arabic, acacia gum, xanthan gum, karaya gum, gellan gum, mannitol, konjac gum, pectin, amidated pectin, microcrystalline cellulose, methylcellulose, hydroxypropylcellulose, methylethylcellulose, sodium carboxymethylcellulose, fatty acid salts (Ca, Na, K and NH4), mono and diglycerides of fatty acids, mono esters and diglycerides with fatty acids, acetic acid esters and fatty acids with glycerol, acetic acid esters of mono- and diglycerides, lactic acid esters of fatty acids with glycerol, lactic acid esters of mono and diglycerides, citric acid esters of fatty acids with glycerol, citric acid esters of mono- and diglycerides, tartaric acid esters of fatty acids with glycerol, tartaric acid esters of mono- and diglycerides, esters of tartaric acid, acetic acid and fatty acids with glycerol, sodium bicarbonate, sodium acid carbonate, potassium carbonate, calcium chloride, maltitol and maltitol syrup, polydextrose and the like.

Examples of sequestrants include, without limitation, citric acid, monosodium citrate, disodium citrate, sodium citrate, trisodium citrate, potassium citrate, tri-potassium citrate, calcium citrate, tri-calcium citrate, sorbitol and sorbitol syrup, acetic acid esters and fatty acids with glycerol, acetic acid esters of mono- and diglycerides, lactic acid esters of fatty acids with glycerol, lactic acid esters of mono- and diglycerides, citric acid esters of fatty acids with glycerol, citric acid esters of mono- and diglycerides, tartaric acid esters of glycerol and fatty acids, tartaric acid esters of mono- and diglycerides, tartaric acid esters, acetic and fatty acids with glycerol, calcium sulfate and the like.

Examples of lubricants include, without limitation, colloidal silicas and the like.

Examples of preservatives include, without limitation, alkyl parabens such as methylparaben, propylparaben, acetic acid, calcium acetate, propionic acid, sodium propionate, calcium propionate, potassium propionate, sodium erythorbate, sodium isoascorbate, sodium benzoate and the like.

Examples of acidity regulators which may be used in order to maintain the food or pharmaceutical compositions in ranges of pH values ranging from 3.0 to 11.0 and include, without limitation, calcium carbonate, acetic acid, calcium acetate, lactic acid, malic acid, fumaric acid, sodium lactate, potassium lactate, calcium lactate, citric acid, monosodium citrate, disodium citrate, sodium citrate, tri-sodium citrate, potassium citrate, tri-potassium citrate, citrate of calcium carbonate, tri-calcium citrate, sodium carbonate, sodium bicarbonate, sodium carbonate, potassium carbonate, ammonium carbonate, ammonium bicarbonate, ammonium acid carbonate, magnesium carbonate, potassium sulfate, sodium hydroxide, potassium hydroxide, calcium hydroxide, ammonium hydroxide, magnesium hydroxide, calcium oxide, gluconic acid, glucono gonadal lactone, calcium gluconate and the like.

Examples of sweeteners include, without limitation, sucralose, aspartame, acesulfame potassium, sodium saccharin, cyclamate, thaumatin, steviosides, rebaudiosides, neohesperidin dihydrochalcone, alitame or mixtures thereof in any proportions.

Another embodiment of the invention provides that the pharmaceutical and food compositions may comprise at least one iron (III) amino acid complex in combination with a second source of iron. The second iron source provides about 0.01 to 200 mg Fe/g of composition and iron from the iron (III) amino acid complex corresponds to about 0.1 to 99.9% of the total iron present in the composition.

Examples of suitable iron sources for the preparation of compositions in combination with the amino acid complexes of iron (III) include, without limitation, ferric hypophosphite, ferric albuminate, ferric chloride, ferrous chloride, ferric sulfate, ferrous sulfate, ammonium ferric sulfate, ammonium ferrous sulfate, ferric citrate, ferrous gluconate, ferrous iodide, ferrous lactate, ferrous fumarate, ferric triglycinate, ferrous bisglycinate, ferrous aspartate glycerate, ferric nitrate, ferric aspartate, ferric hydroxide, ferrous hydroxide, ferric hydroxide, ferrous oxide, ferric oxide, metallic iron, ferric ascorbate, ferrous formate, ferrous acetate, ferrous malate, ferrous glutamate, iron glycine sulfate, soluble ferric pyrophosphate, ferric subsulfate, sodium ferric citrate, sodium iron edetate, ferric formate, ferric ammonium oxalate, potassium ferric oxalate, sodium ferric oxalate, ferric peptonate, among other forms of iron and their combinations.

Another embodiment of the present invention provides the use of iron (III) amino acid complexes of interest in the preparation of foods or drugs or as a nutritional additive for the prophylaxis and/or therapeutic and non-therapeutic treatment of iron deficiencies in humans and animals.

In either case, the iron (III) amino acid complexes are used in nutritionally effective amounts, and in general are preferably used in quantities not higher than the nutritional requirement of iron for the individuals to be supplemented, per dose of food or medicine. In the case of medicines for the treatment of humans, iron requirements can vary from 5 to 1000 mg iron/dose and in the case of food, doses may vary from 0.01 to 20 mg iron/dose. In the case of treatment of animals, iron requirements may vary from 1 to 1000 mg iron/dose or 1 to 1000 ppm iron/kg feed.

It should be noted that the levels added to diets, as defined above, may vary significantly, since the iron levels employed depend on the treatment time during the life cycle of individuals as well as their physiological conditions. Therefore, such values cannot be considered as limiting the scope of the invention.

When the dosage form of the composition of the present invention is presented in solid form for administration through the oral route, such form may be coated or non-coated tablets, capsules, powders, granules or dragees.

In the case of solid forms, the iron (III) amino acid complexes or the food and pharmaceutical compositions of the invention may be combined with a pharmaceutically acceptable inert carrier, such as lactose, calcium carbonate, starch, sucrose, glucose, cellulose derivatives, magnesium stearate, dicalcium phosphate, calcium sulfate, mannitol, sorbitol and the like. Further, when desired or necessary, suitable binders, lubricants, disintegrating agents and coloring agents may also be incorporated into the blend.

Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants that can be used in these dosage forms include sodium oleate, sodium stearate, magnesium stearate, sodium benzoate, sodium acetate, sodium chloride and the like. Disintegrators include, without limitation, starch, cellulose derivatives, agar, bentonite, xanthan gum and the like.

The food and pharmaceutical compositions according to the present invention may also be administered in the form of liposome delivery systems or coupled to soluble or partially soluble polymers, as drug delivery carriers.

For oral administration in liquid forms, the food and pharmaceutical compositions of the invention may be further combined with any oral and pharmaceutically or nutritionally acceptable inert carrier.

Generally, water, a suitable oil, alcoholic solutions, saline solution, aqueous fructose, aqueous sorbitol, aqueous dextrose (glucose), sugar solutions and glycols such as propylene glycol or polyethylene glycols and phosphate buffer are suitable carriers among others which may be selected for each particular use by those skilled in the art.

A few illustrative examples of preparation and use of the compounds of interest of this invention and compositions containing them are mentioned below, again emphasizing that they do not impose any limitation on the scope of the invention other than those set forth in the appended claims.

Also shown are examples of methods for the treatment of plants, which also should not be considered as limiting of this invention, since various variations may be practiced or performed by those skilled in the art in a variety of ways, it being understood that the examples mentioned have the purpose of description and not of limitation.

Example 1

115 g of iron bisglycinate, 32 g of glycine and 5 g of tartaric acid are each added to 350 ml of distilled water in a glass flask. The mixture is heated to 90° C. and held at that temperature for 1 h under a constant flow of oxygen. After this period, 1 g of sodium hydroxide is added in the reaction medium to pH 5.8. Thereafter, and after the process control check for the absence of iron (II) in the reaction medium, 100 ml of solvent are removed under reduced pressure and 250 ml of ethanol are added. The resulting product is separated by filtration and oven dried at 100° C.

Example 2

100 g of iron bismethioninate, 25 g of methionine and 10 g of citric acid are added to 350 ml of distilled water in a glass flask. The mixture is heated to 60° C. and maintained at that temperature for 2 h under a constant flow of oxygen. After this time, 1.4 g of potassium hydroxide is added in the reaction medium to pH 4.7. Thereafter, and after the process control check for the absence of iron (II) in the reaction medium, 100 ml of solvent are removed under reduced pressure and 250 ml of ethanol are added. The resulting product is separated by filtration and oven dried at 100° C.

Example 3

265 g of ferrous citrate, 225 g of glycine and 80 g of 50% sodium hydroxide in are added to 1470 ml of distilled water in a glass flask. The mixture is heated to 50° C. and maintained at that temperature for 30 min under a constant flow of oxygen. Then, after the process control check for the absence of iron (II) in the reaction medium, the reaction mixture is cooled and the solution obtained is dried in a spray drier to obtain a product having pH 9.2 when dissolved in water.

Example 4

265 g of ferrous citrate and 70 g of ammonium hydroxide solution are added to 1400 ml of distilled water in a glass flask. The mixture is heated to 50° C. and maintained at that temperature for 30 min under a constant flow of oxygen. Next, 300 g of glycine is added and the reaction mixture is kept under stirring for 30 min. After verification by process control of the absence of iron (II) in the reaction medium, the solution obtained at pH 8.8 is dried in drier spray.

Example 5

265 g of ferrous citrate, 400 g of aspartic acid and 28 g of calcium oxide are added to 100 ml of distilled water in a glass flask. The mixture is heated under reflux and held at that temperature for 1 h under a constant flow of oxygen. Then, after verification by process control of the absence of iron (II) in the reaction medium, the solution obtained with pH 7.5 is cooled and dried in a drier spray.

Example 6

265 g of ferrous citrate, ferrous bisalaninate 310 g, 415 g of alanine and 70 g of ammonium hydroxide solution are added to 1400 ml of distilled water in a glass flask. The mixture is heated to 50° C. and maintained at this temperature for 30 min under a constant flow of oxygen. Next, and after the verification process by control of the absence of iron (II) in the reaction medium, the solution obtained is dried in a spray drier.

Example 7

270 g of ferric chloride hexahydrate and 130 g of sodium hydroxide are added to 500 ml of water in a glass flask. Next, 225 g of glycine and 30 g of malic acid are added and the mixture is kept under stirring until the solids are completely dissolved. The obtained solution is then ultrafiltered for separation of the iron (III) glycinate complex and the solution obtained containing the complex is dried in a spray drier.

Example 8

270 g of ferric chloride hexahydrate and 130 g of sodium hydroxide are added to 500 ml of water in a glass flask. Next, 225 g of glycine and 30 g of malic acid are added and the mixture is kept under stirring until the solids are completely dissolved. The solution obtained is then ultrafiltered for separation of the iron (III) glycinate complex, which is obtained after removal of the solvent under reduced pressure and precipitation by the addition of an equal volume of ethanol.

Example 9

482 g of ammonium ferric sulfate and 112 g of sodium oxide are added to 2000 ml of water in a glass flask and the mixture is kept under stirring at room temperature for 20 min. Next, 440 g of glutamic acid, 20 g of malic acid, 4 g of potassium hydroxide are added and the mixture and is kept under stirring until complete dissolution of the solids. The reaction mixture is then filtered for separation of the iron (III) glutamate complex and the product is obtained by drying in a spray drier.

Example 10

Hard candies with essentially no undesired taste of iron containing the iron amino acid complex described in Example 1 are prepared by combining, cooking and hot molding of the components listed below in the following proportions:

| Component | Content (%, w/w) |
| --- | --- |
| Glucose syrup | 65-55 |
| Saccharose | 31.9-43.5 |
| Iron complex | 0.1-0.05 |
| Acidifier | 0.5-0.2 |
| Aroma and color | 0.5-0.2 |
| Water | qsp |

Example 11

Fruit concentrates with essentially no undesired taste of iron used for preparing yogurts containing the amino acid iron complex described in Example 2 are prepared by combining and cooking the components listed below in the following proportions:

| Component | Content (%, w/w) |
| --- | --- |
| Fruit | 70-60 |
| Saccharose | 20-30 |
| Iron complex | 0.1-0.05 |
| Acidifier | 1.0-0.5 |
| Preservatives | 0.1-0.01 |
| Aroma and color | 0.5-0.2 |
| Water | qsp |

Example 12

Syrups with essentially no undesired taste of iron in the form of a liquid composition are prepared by combining the following components, wherein the iron complex of Example 3 is initially dissolved in water:

| Component | Content (%, w/w) |
| --- | --- |
| Sorbitol 70% | 25-35 |
| Propylene glycol | 30-50 |
| Iron complex | 0.1-0.05 |
| Sequestrant | 0.1-0.2 |
| Thickener | 0.1-0.5 |
| Preservatives | 0.1-0.2 |
| Aroma and color | 0.1-0.4 |
| Water | qsp |

Example 13

Food supplements with essentially no undesired taste of iron in the form of preparations for powdered drinks are made by combining the following components in a Y-type mixer:

| Component | Content (%, w/w) |
| --- | --- |
| Calcium caseinate | 40-45 |
| Concentrated whey protein | 8-16 |
| Isolated soy protein | 8-16 |
| Sunflower oil | 2-5 |
| Iron complex | 0.1-0.3 |
| Fructose | 20-30 |
| Saccharose | 10-20 |
| Zinc bisglycinate | 0.01-0.02 |
| Aroma and color | 0.2-0.5 |
| Maltodextrin | qsp |

Example 14

Beverages of fruit nectar type with essentially no undesired taste of iron are prepared by combining the following components utilizing any of the iron complexes described in Examples 1 to 10:

| Component | Content (%, w/w) |
| --- | --- |
| Fruit concentrate | 10-20 |
| Iron complex | 0.01-0.25 |
| Xanthan gum | 0.2-0.5 |
| Sucralose | 0.5-1.0 |
| Preservatives | 0.1-0.2 |
| Sequestrantes | 0.01-0.03 |
| Stabilizers | 0.01-0.3 |
| Acidifiers | 0.5-1.0 |
| Antioxidantes | 0.05-0.2 |
| Aroma and color | 0.1-0.7 |
| Water | qsp |

Example 15

Suspensions in oral form with essentially no undesired iron taste are prepared by combining the following components utilizing any of the iron complexes described in Examples 1 to 10:

| Component | Content (%, w/w) |
| --- | --- |
| Iron complex | 0.1-0.05 |
| Preservative | 0.001-0.5 |
| Thickener | 10-0.01 |
| Sweetener | 1.0-0.01 |
| Surfactants | 10-0.01 |

| Component | Content (%, w/w) |
| --- | --- |
| Aroma and color | 0.5-0.2 |
| Antifoam | 0.2-0.01 |
| Solvent 1 | 80-1.0 |
| Solvent 2 | qsp |

Example 16

Chewable balls with essentially no undesired taste of iron containing any of the iron amino acid complexes described in Examples 1 to 10 are prepared by combining, cooking and hot molding of the components listed below in the following proportions:

| Component | Content (%, w/w) |
| --- | --- |
| Glucose syrup | 70-50 |
| Xylitol | 40-30 |
| Iron complex | 0.5-0.05 |
| Acidifier | 1.5-0.1 |
| Preservative | 0.2-0.01 |
| Aroma and color | 1.0-0.01 |
| Water | qsp |

Example 17

Whole fortified milks without any undesired taste or color containing any of iron amino acid complexes described in Examples 1 to 10 are prepared by combining in a tank, with stirring, the components listed below in the following proportions:

| Component | Content (%, w/w) |
| --- | --- |
| Iron complex | 0.1-0.05 |
| Sodium Ascorbate | 0.05-0.01 |
| Vitamina D 100,000 IU | 0.002-0.001 |
| Vitamina A 325,000 IU | 0.004-0.002 |
| Whole milk | qsp |

Example 18

Whole Milk powder fortified without any flavor or undesired coloration containing any of the iron amino acid complexes described in Examples 1 to 10 are prepared by combining in a tank, with stirring, the components listed below in the following proportions and subsequent spray drying:

| Component | Content (%, w/w) |
| --- | --- |
| Iron complex | 0.1-0.05 |
| Sodium ascorbate | 0.05-0.01 |
| Vitamina D 100,000 IU | 0.002-0.001 |
| Vitamina A 325,000 IU | 0.004-0.002 |
| Whole milk | qsp |

Example 19

Preparations for powdered drinks with essentially no undesired taste of iron are made by combining any of the iron amino acid complexes described in Examples 1 to 10 and the components listed below in a Y-type mixer:

| Component | Content (%, w/w) |
|---|---|
| Iron complex | 1.0-0.5 |
| Aroma | 20-10 |
| Color | 1.5-0.5 |
| Zinc oxide | 0.5-0.1 |
| Acidity Regulator | 20-10 |
| Acidifier | 10-5 |
| Premix of vitamin C, vitamin B3, vitamin B12, folic acid* | 4.0-2.0 |
| Carrier | qsp |

*Amount sufficient to reach 100% of the RDI of each component after dissolving the powder prepared in 200 ml of liquid.

The invention claimed is:

1. A pharmaceutical composition comprising an iron amino acid compound having a molecular formula:

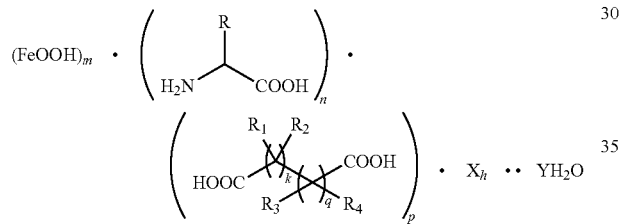

where:
R is —H or the side chain of an essential or nonessential amino acid selected from the group consisting of alanine, phenylalanine, leucine, isoleucine, proline, hydroxyproline, arginine, methionine, aspartic acid, glutamic acid, valine, threonine, isothreanine, histidine, tryptophan, serine, glutamine, and mixtures thereof;
R1 is H or —OH;
R2 is —H or —CH2COOH;
R3 is —H or —OH;
R4 is H;
k is equal to 0 or 1; wherein
  if k is equal to zero, q is between 1 and 3;
  if k is equal to 1, q is between 0 and 3;
X is —Na, —K, —Ca, —Mg or —NH4;
Y is between 0 and 20;
the molar ratio of m:n ranges from 1:0.5 to 1:10;
the molar ratio of m:p ranges from 1:0.1 to 1:1; and
the molar ratio m:h ranges from 0.001 to 5.0;
and at least one pharmaceutically acceptable carrier;
wherein the composition comprises:
  iron from 0.01 to 200 mg/g of the composition from one or more sources of iron, whereby at least one source of iron is an amino acid complex;
  0.0 to 99% w/w of a nutrient;
  0.001 to 99% w/w of a pharmaceutically or nutritionally acceptable inert carrier;
  0.0 to 99% w/w sweetener;
  0.001 to 20% w/w flavoring agents;
  0.001 to 1% w/w colorants;
  0.0 to 20% w/w of at least one additive selected from the group consisting of anti-humectants, humectants, antioxidants, thickeners, stabilizers, sequestrants, lubricants, preservatives, acidity regulators, and combinations thereof.

2. The composition according to claim 1 comprising 0.01 to 5% of the at least one additive.

3. A pharmaceutical composition in the form of an aqueous solution comprising an iron amino acid compound having a molecular formula:

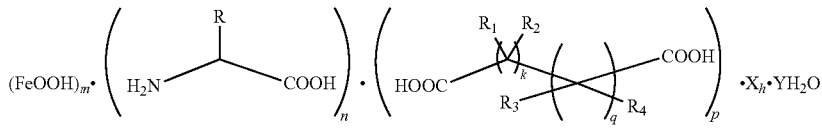

where:
R is —H or the side chain of an essential or nonessential amino acid selected from the group consisting of alanine, phenylalanine, leucine, isoleucine, proline, hydroxyproline, arginine, methionine, aspartic acid, glutamic acid, valine, threonine, isothreanine, histidine, tryptophan, serine, glutamine, and mixtures thereof;
R1 is H or —OH;
R2 is —H or —CH2COOH;
R3 is —H or —OH;
R4 is H;
k is equal to 0 or 1; wherein
  if k is equal to zero, q is between 1 and 3;
  if k is equal to 1, q is between 0 and 3;
X is —Na, —K, —Ca, —Mg or —NH4;
Y is between 0 and 20;
the molar ratio of m:n ranges from 1:0.5 to 1:10;
the molar ratio of m:p ranges from 1:0.1 to 1:1; and
the molar ratio m:h ranges from 0.001 to 5.0;
and at least one pharmaceutically acceptable carrier;
wherein the composition comprises:
  0.01 to 10% w/w iron (III)
  0.02 to 3% w/w of an organic acid;
  0.02 to 25% w/w of an amino acid;
  0.001 to 5% w/w of a cation; and
  40 to 99.9% w/w water.

4. The composition according to claim 3 wherein the organic acid is selected from the group consisting of citric, oxalic, tartaric, aspartic, malic, succinic, glutamic and adipic.

5. The composition according to claim 4, wherein the organic acid is citric acid.

6. The composition according to claim 3, wherein the amino acid is selected from the group consisting of glycine, L-lysine, L-alanine, L-phenylalanine, L-leucine, L-isoleucine, L-proline, L-hydroxyproline, L-arginine, L-ornithine, L-methionine, L-aspartic acid, L-glutamic acid, L-valine, L-threonine, L-isothreonine, L-histidine, L-tryptophan, L-serine, L-glutamine, L-citrulline, their enantiomeric forms, and mixtures thereof.

7. The composition according to claim 6, wherein the amino acid is glycine.

8. The composition according to claim 3, wherein the cation is selected from the group consisting of sodium, potassium, calcium, magnesium and ammonium.

9. The composition according to claim 8, wherein the cation is sodium.

10. A pharmaceutical composition comprising an iron amino acid compound having a molecular formula:

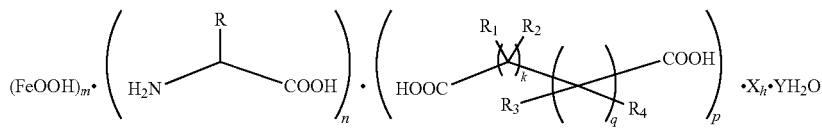

where:
- R is —H or the side chain of an essential or nonessential amino acid selected from the group consisting of alanine, phenylalanine, leucine, isoleucine, proline, hydroxyproline, arginine, methionine, aspartic acid, glutamic acid, valine, threonine, isothreanine, histidine, tryptophan, serine, glutamine, and mixtures thereof;
- R1 is H or —OH;
- R2 is —H or —CH2COOH;
- R3 is —H or —OH;
- R4 is H;
- k is equal to 0 or 1; wherein
  - if k is equal to zero, q is between 1 and 3;
  - if k is equal to 1, q is between 0 and 3;
- X is —Na, —K, —Ca, —Mg or —NH4;
- Y is between 0 and 20;
- the molar ratio of m:n ranges from 1:0.5 to 1:10;
- the molar ratio of m:p ranges from 1:0.1 to 1:1; and
- the molar ratio m:h ranges from 0.001 to 5.0;

and at least one pharmaceutically acceptable carrier;
wherein the composition further comprises:
- 0.001 to 99% w/w of a nutrient;
- 0.001 to 99% w/w sweetener;
- 0.001 to 20% w/w flavoring agents;
- 0.001 to 1% w/w colorants; and
- 0.0 to 20% w/w of at least one additive selected from anti-humectantes, humectants, antioxidants, thickeners, stabilizers, sequestrants, lubricants, preservatives, acidity regulators, and combinations thereof.

11. The composition according to claim 1, wherein the nutrients are selected from the group consisting of minerals, vitamins, omega 3, omega 6, omega 9 vegetable oils or their derivatives, lycopene, lutein, carnitine, creatine, plant extracts, amino acids, peptides, proteins and mixtures thereof in any proportions.

12. The composition according to claim 10 comprising 0.01 to 5% of the at least one additive.

* * * * *